United States Patent
Sato

(10) Patent No.: US 8,191,471 B2
(45) Date of Patent: Jun. 5, 2012

(54) METHOD FOR INSPECTING PRINT, APPARATUS FOR INSPECTING PRINT, AND PRINTER

(75) Inventor: Toshimichi Sato, Shizuoka (JP)

(73) Assignee: Yamaha Hatsudoki Kabushiki Kaisha (JP)

( * ) Notice: Subject to any disclaimer, the term of this patent is extended or adjusted under 35 U.S.C. 154(b) by 847 days.

(21) Appl. No.: 12/298,305

(22) PCT Filed: Mar. 30, 2007

(86) PCT No.: PCT/JP2007/057092
§ 371 (c)(1),
(2), (4) Date: Oct. 24, 2008

(87) PCT Pub. No.: WO2007/125722
PCT Pub. Date: Nov. 8, 2007

(65) Prior Publication Data
US 2009/0174747 A1    Jul. 9, 2009

(30) Foreign Application Priority Data
Apr. 28, 2006 (JP) ................................. 2006-125834

(51) Int. Cl.
*B41L 13/16* (2006.01)
*B41F 15/08* (2006.01)
(52) U.S. Cl. .................. 101/123; 101/484; 101/129

(58) Field of Classification Search ................ 101/114, 101/123, 129, 484
See application file for complete search history.

(56) References Cited

U.S. PATENT DOCUMENTS
6,634,290 B1 * 10/2003 Shimizu et al. ............. 101/129
2002/0015780 A1 * 2/2002 Holm et al. .................... 427/8

FOREIGN PATENT DOCUMENTS
JP          6027033       2/1994
JP          8052952       2/1996

* cited by examiner

*Primary Examiner* — Leslie J Evanisko
(74) *Attorney, Agent, or Firm* — Studebaker & Brackett PC; Donald R. Studebaker

(57) ABSTRACT

A print inspection device is provided with a camera for picking-up an image of a substrate to be processed after a paste is printed on the substrate through a mask sheet by a printer, a measured value calculating a measured value of a printed paste area based on the picked-up image of the substrate, a setting means for setting a standard range for working state judgment of the area, and a comparing and judging means for comparing the measured value with the standard range and for judging whether the printer is in a normal working state or not depending on whether the measured value is in the standard range or not. The setting means sets the standard range to a less paste amount side for a predetermined period of time after the mark sheet is cleaned up than for other periods of time.

16 Claims, 7 Drawing Sheets

METHOD FOR INSPECTING PRINT, APPARATUS FOR INSPECTING PRINT, AND PRINTER

TECHNICAL FIELD

The present invention relates to a method and an apparatus for efficiently inspecting a print state after a printed wiring board and a mask sheet are superimposed and a paste, such as a cream solder, is printed on the printed wiring board via openings formed in the mark sheet.

BACKGROUND ART

Conventionally, a printed circuit board is manufactured as follows: while a printed wiring board bearing a circuit pattern is transported, a paste, such as a cream solder and a conductive paste, is first printed by a printer on the printed wiring board at points onto which components are to be mounted, and then components are successively mounted onto the printed points by a surface mounting apparatus (hereinafter, referred to simply as mounting apparatus).

The printer is configured to superimpose a mask sheet on a printed wiring board set, for example, on the stage and to press paste supplied on the mask sheet using a squeegee, so that paste is printed on the printed wiring board at predetermined positions via openings formed in the mask sheet. After the printing, an image of the printed wiring board is taken by a print inspection apparatus incorporated in the printer or a print inspection apparatus disposed downstream of the printer, and the print state is inspected on the basis of the image.

The print inspection apparatus determines whether the product is acceptable or unacceptable by measuring a quantity in connection with an amount of paste printed on the printed wiring board to be inspected, for example, an area of printed paste, and then determining whether the measurement value falls within a reference range set in advice according to designed values of the mask sheet or the like.

Also, as is disclosed in Japanese Patent Unexamined Publication No. HEI6-27033, not only to determine whether the product is acceptable or unacceptable, but also to determine a tendency (smearing tendency and fainting tendency) of print state even when measurement value falls within the range of an acceptable product, an absolute reference value used to determine whether the product is acceptable or unacceptable and an operative condition determination reference value (reference value used to determine a tendency of print state) to be set in a narrower range are set in advance, and the measurement value of a pasted area is compared with these reference values.

According to the apparatus configured as above, by judging a printing state change caused by an abnormality in the printer or the like apart from the determination as to whether the product is acceptable or unacceptable, and adjusting the printer in response to such a change, it is expected that the occurrence of an unacceptable product can be prevented in advance. Further, in order to deal with an error in the area of openings of the mask sheet or the like, the apparatus of the cited reference is configured to check a measurement value distribution on the basis of measurements conducted many times and to change the operative condition determination reference according to the distribution.

Repetitive performance of printing operation on printed circuit boards by the printer makes a considerable amount of paste adhere onto the mask sheet, so that clogging or the like readily occurs. Such being the case, the mask sheet is usually cleaned at adequate intervals. According to the examination by the inventor, an amount of paste printed on a printed wiring board on which components are to be mounted is likely to differ between a time immediately after cleaning of the mask sheet and the other time even when no abnormality occurs in the printer. To be more specific, the amount of paste tends to decrease immediately after cleaning.

In a case where a determination reference to check an operative condition change caused by an abnormality in the printer or the like is set, if the printer is managed according to the same determination reference, the determination reference is required to have a normal range for the time immediately after cleaning and a normal range for the other time. This, however, raises a problem of lowering the reliability in detection of an abnormality in the printer. Even if the operative condition determination reference is changed according to the distribution of measurement values as is disclosed in the cited reference, the operative condition determination reference is adjusted merely according to the distribution of measurement values falling in a wide range including the time immediately after cleaning and the other time. It is therefore difficult to make a suitable determination for the time immediately after cleaning and the other time.

DISCLOSURE OF THE INVENTION

The invention has been worked out in view of the above-mentioned problems, and has an object to make it possible to evaluate an operative condition change caused by an abnormality in a printer or the like, and moreover, to make such evaluation suitably for a time immediately after cleaning and for the other time.

In order to achieve the above and other objects, a print inspection method according to the invention is adapted for inspecting a paste print state on a printed wiring board after a paste is printed on the printed wiring board via a mask sheet by a printer equipped with the mask sheet. The method includes: a measuring step of measuring a quantity in connection with an amount of paste printed on the printed wiring board; and a determining step of comparing a measurement value obtained by the measurement with a reference range for operative condition determination to determine whether an operative condition of the printer is normal depending on whether the measurement value falls within the reference range. In the determining step, a special reference range is used for the operative condition determination in a particular time immediately after cleaning of the mask sheet is performed, the special reference range being set for a smaller amount of paste than that for which a normal reference range is set in the other time than the particular time immediately after cleaning.

According to this method, the quantity is measured after the paste is printed on the printed wiring board and whether the operative condition of the printer is normal is determined depending on whether the measurement value falls within the reference range for operative condition determination. In this instance, because the reference range for operative condition determination is shifted between the time immediately after cleaning and the other time, it is possible to distinguish between a case where the measurement value changes because the current moment is immediately after cleaning while the printer is operating normally and a case where the measurement value changes because the operative condition of the printer is out of the normal state. It thus becomes possible to judge an operative condition change more appropriately.

Also, a print inspection apparatus according to the invention is adapted for inspecting a paste print state on a printed wiring board after paste is printed on the printed wiring board via a mask sheet by a printer equipped with the mask sheet. The apparatus includes: a measuring device for measuring a quantity in connection with an amount of paste printed on the printed wiring board; a reference range setting device for setting a reference range for operative condition determination in terms of the quantity; and a comparing and determining device for comparing a measurement value obtained by the measuring device with a reference range set by the reference range setting device to determine whether an operative condition of the printer is normal depending on whether the measurement value falls within the reference range. The reference range setting device is configured to selectively set a normal reference range and a special reference range for operative condition determination. The special reference range is set for a smaller amount of paste than that for which the normal reference range is set. The special reference range is set for a particular time immediately after cleaning of the mask sheet is performed, and the normal reference range is set for the other time than the particular time.

According to this apparatus, the print inspection method described above can be automated and performed effectively.

Further, a printer according to the invention includes: a mask sheet; a print stage located below the mask sheet and configured to support a printed wiring board in a manner so as to allow the printed wiring board to move up and down; a squeegee unit located above the mask sheet and configured to apply a paste; a device for carrying the printed wiring board in and out from the print stage; and the print inspection apparatus described above. After printing, the paste print state of the printed wiring board on the print stage is inspected.

According to this configuration, the print state of the printed wiring board is inspected and the operative condition of the printer is determined according to the print inspection method described above until the printed wiring board is carried out after the printing is performed. Accordingly, a series of operations from the printing of a printed wiring board to the determination of the operative condition of the printer can be performed within the printer.

BEST MODE FOR CARRYING OUT THE INVENTION

The invention will be described with reference to the drawings.

Figure 1:
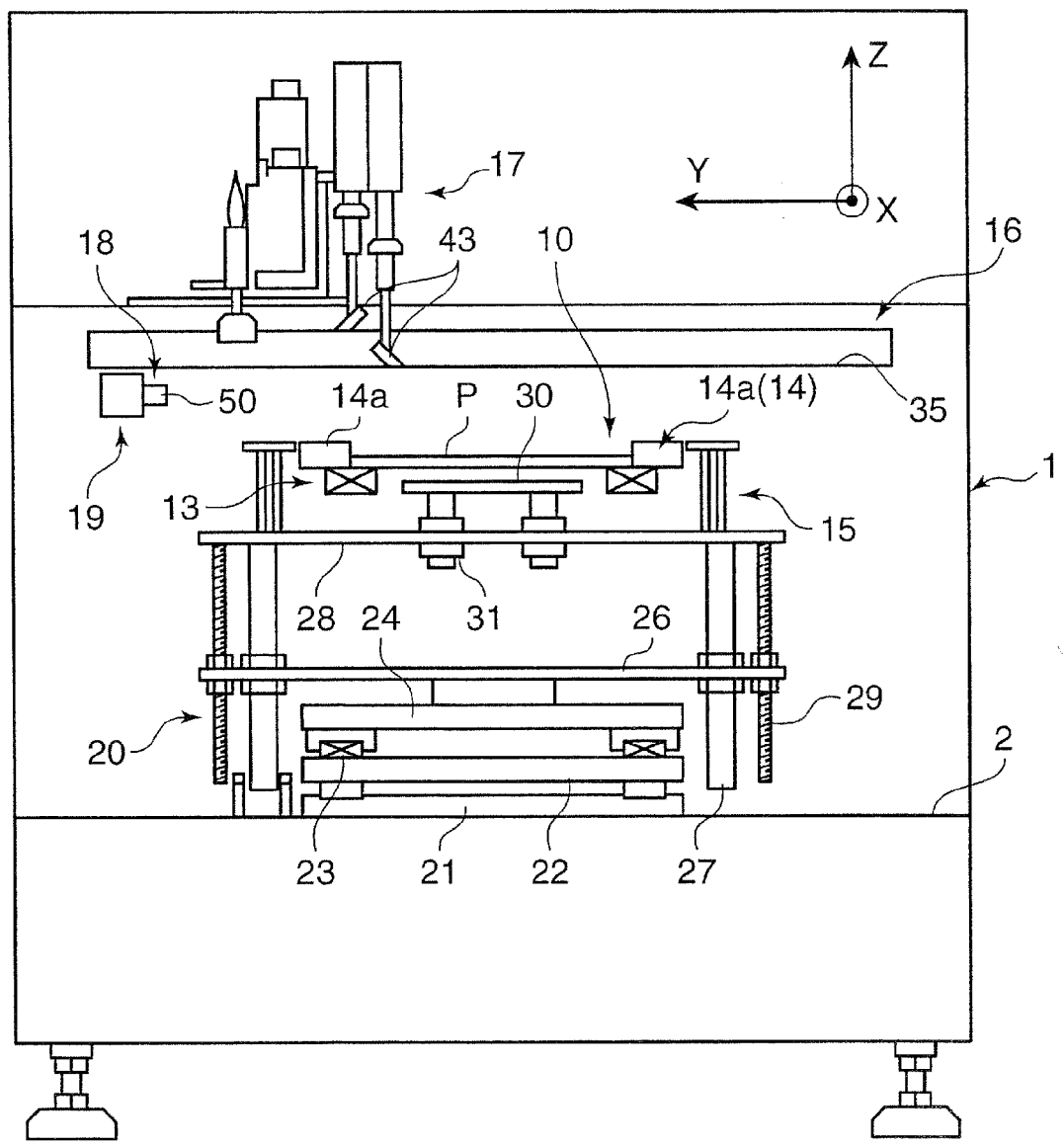
FIG. 1 is a side view showing a screen printer according to an embodiment of the invention.
Figure 2:
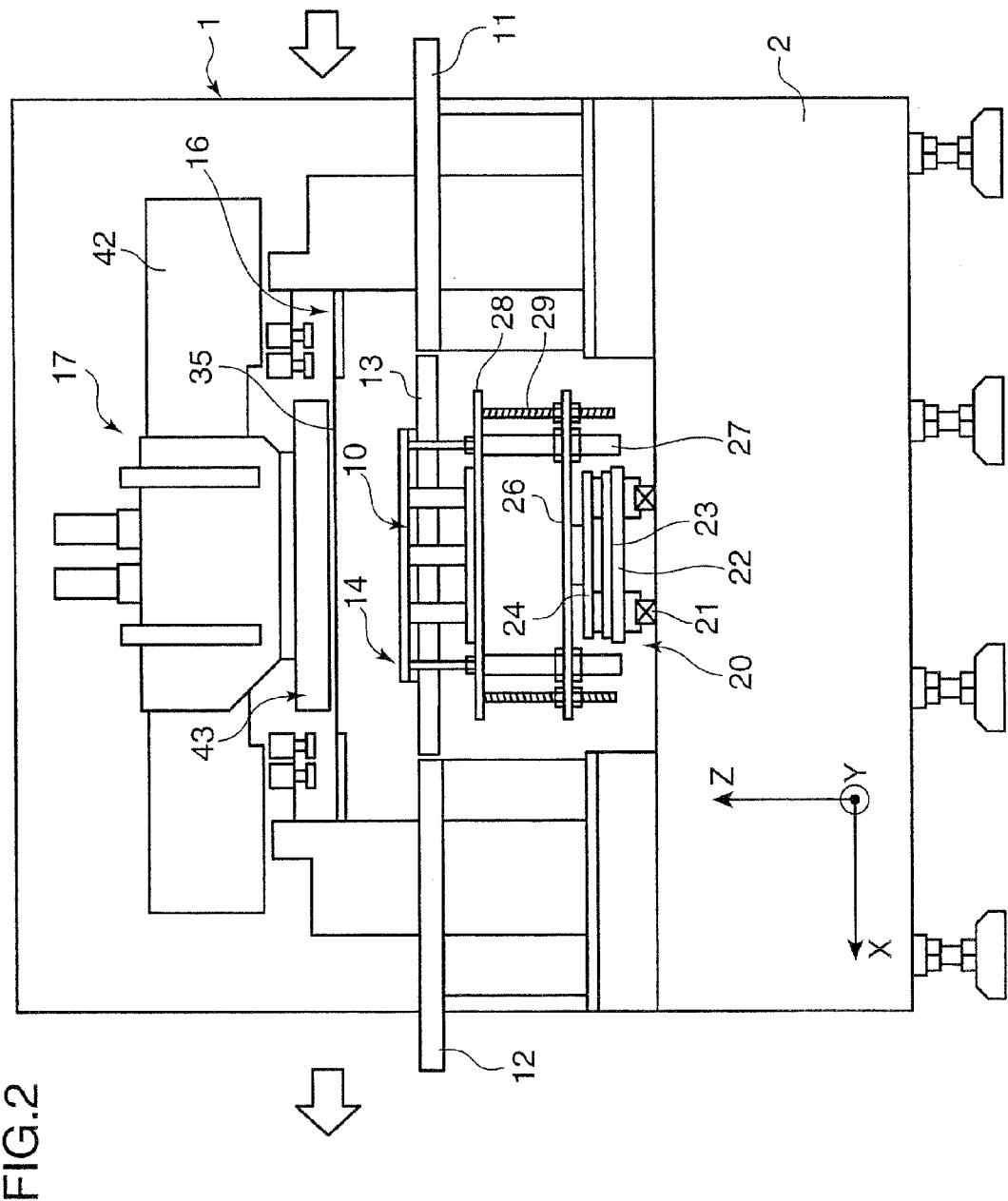
FIG. 2 is a front view showing the screen printer.

FIG. 1 and FIG. 2 schematically show a screen printer 1. FIG. 1 is a side view of a major portion of the screen printer 1, and FIG. 2 is a front view in a state where a cover is removed.

As are shown in these drawings, a print stage 10 is provided on a base stand 2 of the screen printer 1 (hereinafter, referred to simply as the printer 1), and an upstream conveyor 11 and a downstream conveyor 12 for carrying a board P to be processed, which is a printed wiring board (hereinafter referred to simply as "board P"), in and out of the print stage 10 are disposed along the transportation line on the both sides with the print stage 10 therebetween. Hereinafter, descriptions will be given on the assumption that a transportation direction of the board P by the conveyors 11 and 12 is the X-axis direction, a direction orthogonal to the X-axis direction on a horizontal plane is the Y-axis direction, and a direction orthogonal to both the X-axis and Y-axis is the Z-axis direction.

The print stage 10 is to hold the board P for positioning the board P with respect to a mask sheet 35 described below from the underside, and is chiefly formed of main conveyors 13, an elevating table 28, a clamp mechanism 14, and so forth described below.

The print stage 10 is supported on a 4-axis unit 20 and is configured to move in the X-axis, the Y-axis, the Z-axis, and the R-axis (rotation about the Z-axis) with the operations of the unit 20.

More specifically, a rail 21 is provided on the base stand 2 within the horizontal plane along the Y-axis direction and a Y-axis table 22 is attached to the rail 21 in a slidable manner. A ball screw mechanism (not shown) provided on the base stand 2 is coupled to the Y-axis table 22, and it is configured in such a manner that the Y-axis table 22 is moved in the Y-axis direction with respect to the base stand 2 by driving the ball screw mechanism.

A rail 23 is provided on the Y-axis table 22 along the X-axis direction, and an X-axis table 24 is attached to the rail 23 in a slidable manner. A ball screw mechanism (not shown) provided on the Y-axis table 22 is coupled to the X-axis table 24, and it is configured in such a manner that the X-axis table 24 is moved in the X-axis direction with respect to the Y-axis table 22 by driving the ball screw mechanism.

An R-axis table 26 is provided in the X-axis table 24 in a rotatable manner about the axial line along the vertical line (in the Z-axis direction), and it is configured in such a manner that the R-axis table 26 is driven to rotate about the Z-axis with respect to the X-axis table 24 by unillustrated driving device.

Slide supporting columns 27 are attached to the R-axis table 26 in a slidable manner along the top-bottom direction (Z-axis direction), and an elevating table 28 is attached to the top portions of the slide supporting columns 27. A ball screw mechanism 29 is provided between the elevating table 28 and the R-axis table 26, and it is configured in such a manner that the elevating table 28 is moved in the Z-axis direction (top-bottom direction) with respect to the R-axis table 26 while it is guided by the slide supporting columns 27 by driving the ball screw mechanism 29.

As has been described, the 4-axis unit 20 is configured to move the print stage 10 in the X-axis, the Y-axis, the Z-axis, and the R-axis (rotation about the Z-axis) by driving the respective tables 22, 24, 26 and 28 separately.

On the elevating table 28, not only a pair of the main conveyors 13 is provided along the X-axis direction, but also the clamp mechanism 14, a positioning mechanism 15, a mount table 30, and so forth are provided. As has been described, the elevating table 28, the main conveyors 13, and so forth together form the print stage 10 to hold the board P.

It is configured in such a manner that the main conveyors 13 move integrally with the elevating table 28 as it moves up and down and they are aligned in the X-axis direction with respect to the upstream conveyor 11 and the downstream conveyor 12 while the elevating table 28 is set at the specific home position (the descent end position as well as the predetermined original position in the X-axis, Y-axis, and R-axis directions). When the elevating table 28 is set at the home position in this manner, the board P is carried in onto the print stage 10 (main conveyors 13) from the upstream conveyor 11 and the board P is carried out from the print stage 10 to the downstream conveyor 12.

The clamp mechanism 14 is to hold the board P fixedly during the operation. It has a pair of clamp pieces 14a capable of coming closer to each other and moving apart from each other in the Y-axis direction and is configured to fix the board P by sandwiching the board P from the both sides in the Y-axis direction using these clamp pieces 14a. The clamp mechanism 14 uses an air cylinder as the driving source and it is configured to be switched between a clamp state where the clamp pieces 14a are in close proximity to each other and a clamp released state where the clamp pieces 14a are spaced apart from each other according to operations of the air cylinder.

Although it is not shown in detail in the drawing, the positioning mechanism 15 is to position the board P by controlling deflection or the like of the board P before the board P is clamped by the clamp mechanism 14.

The mount table 30 is to support the board P by lifting up the board P on the main conveyors 13 from below. The mount table 30 is supported on the elevating table 28 by slide supporting columns 31 so that it can move up and down and coupled to a ball screw mechanism (not shown) provided between the table 30 and the elevating table 28. It is configured in such a manner that the mount table 30 is moved in the Z-axis direction (top-bottom direction) with respect to the elevating table 28 by the driving of the ball screw mechanism.

Meanwhile, a mask holding unit 16, a squeegee unit 17, an imaging unit 18, a cleaner 19, and so forth are disposed above the print stage 10 and the like.

Figure 3:
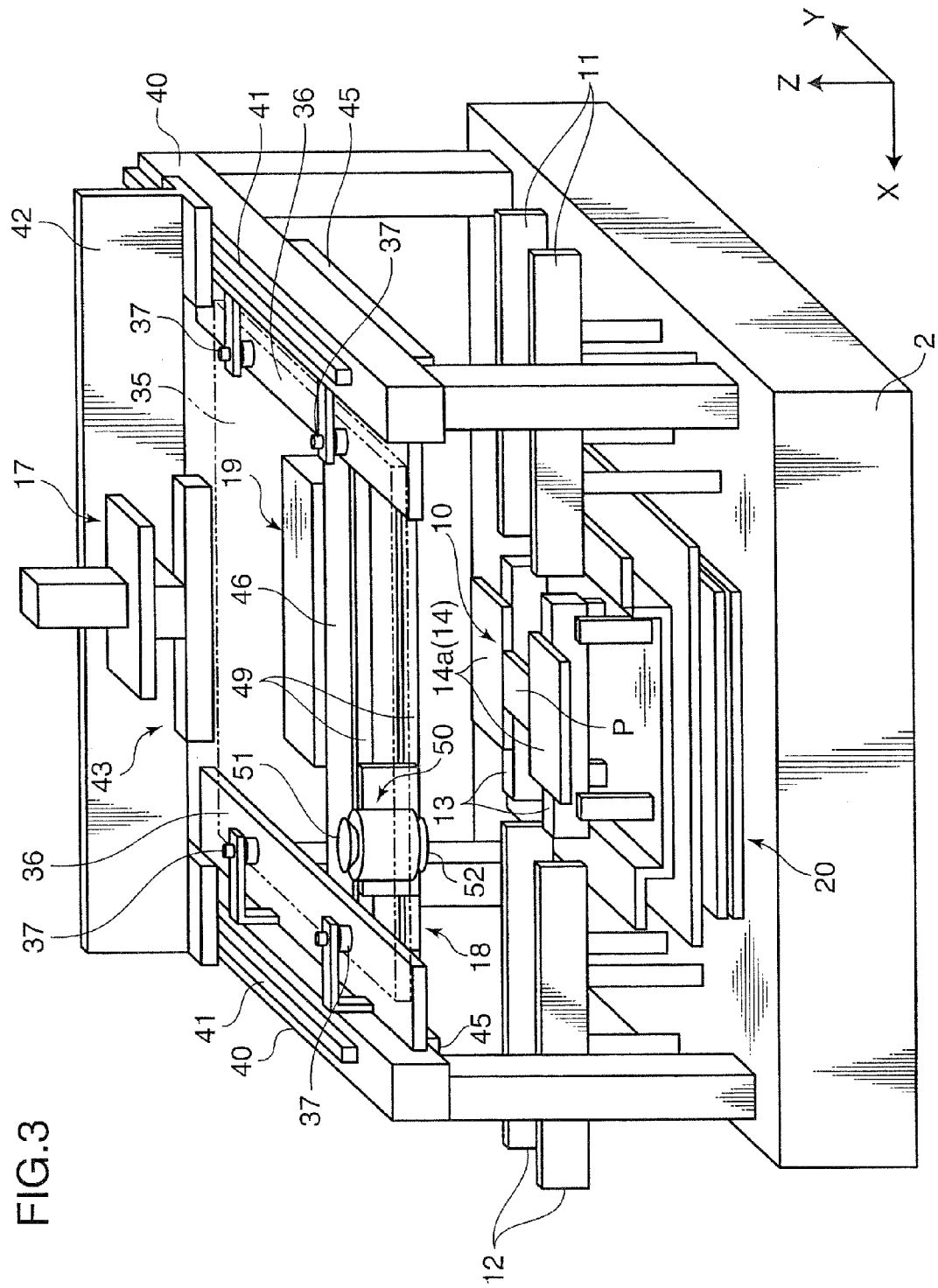
FIG. 3 is a perspective view showing the screen printer.
Figure 4:
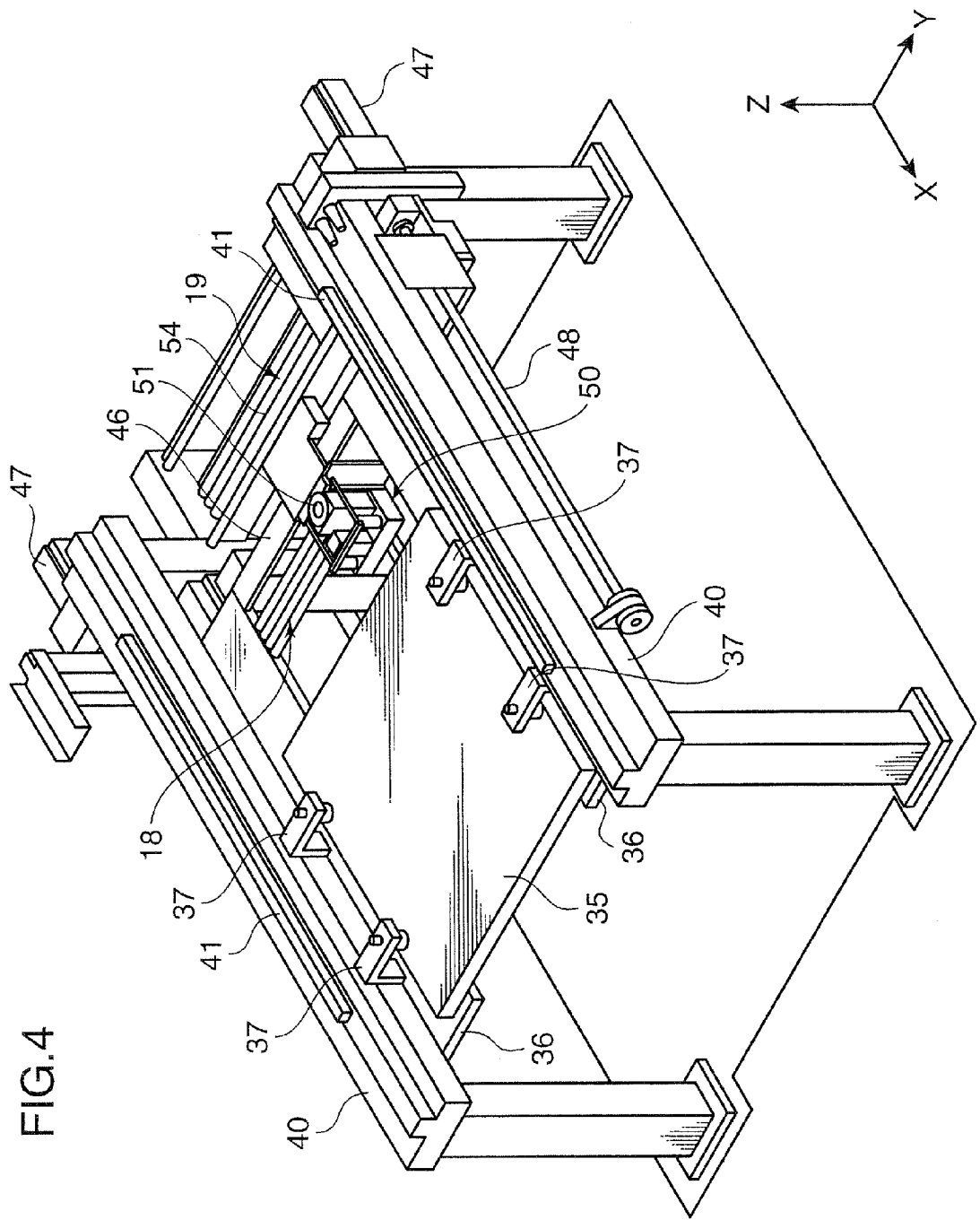
FIG. 4 is a partial perspective view showing portions of an imaging unit and a cleaner in the screen printer.

The mask holding unit 16 is to hold the mask sheet 35. As are shown in FIG. 3 and FIG. 4, the mask holding unit 16 has mask holding stands 36 respectively fixed to a pair of elevated frames 40 supported on the base stand 2. It is configured in such a manner that the mask sheet 35 is clamped by mask clamps 37 provided in the respective mask holding supports 36 in a state where the mask 35 is stretched horizontally above the print stage 10.

The squeegee unit 17 is to spread a paste, such as a cream solder and a conductive paste, supplied on the mask sheet 35 from an unillustrated nozzle by rolling (kneading) the paste on the mask sheet 35.

The squeegee unit 17 is fixedly attached to the respective frames 40 and inserted into rails 41 extending in the Y-axis direction so as to bridge between these rails 41, and includes a beam 42 moved in the Y-axis direction by an unillustrated driving mechanism, a pair of squeegees 43 and 43 to spread the paste over the mask sheet 35, and elevating mechanisms provided in the beam 42 to move up and down these squeegees 43 and 43 separately. It is configured in such a manner that the paste is spread over the mask sheet 35 during the printing by allowing the squeegees 43 and 43 to slide alternately along the surface of the mask sheet 35 while the beam 42 is reciprocating in the Y-axis direction.

The imaging unit 18 is to take images of the board P and the mask sheet 35 and provided below the mask holding unit 16.

The imaging unit 18 includes a camera head 50 integrally provided with a mask recognition camera 51 and a board recognition camera 52 and a driving mechanism to move the camera head 50. It is configured in such a manner that images of the mask sheet 35 and the board P are taken by moving the camera head 50 in the X-axis direction and in the Y-axis direction in a planar manner.

More specifically, a pair of rails 45 extending in the Y-axis direction is provided on the lower surface of the corresponding frames 40, and a beam 46 extending in the X-axis direction is inserted into these rails 45 in a movable manner while it is supported on the frames 40. In addition, ball screw shafts 48 driven to rotate by corresponding motors 47 are threaded into unillustrated nut portions of the beam 46. Also, a pair of rails 49 extending in the X-axis direction is provided in the beam 46. The camera head 50 is inserted into these rails 49 in a movable manner and an unillustrated ball screw shaft mounted on the beam 46 and driven by a motor is threaded into an unillustrated nut portion of the camera head 50. In other words, it is configured in such a manner that the beam 46 moves in the Y-axis direction with respect to the frames 40 and the camera head 50 moves in the X-axis direction with respect to the beam 46 in association with rotations of the corresponding ball screw shafts, which allows the camera head 50 to move between a printing operation area and an evacuation area on the outside in a planar manner.

Each of the mask recognition camera 51 and the board recognition camera 52 is comprised of a CCD camera or the like equipped with a lighting device. Of these cameras, the mask recognition camera 51 is to take an image of a fiducial mark for position recognition provided on the lower surface of the mask sheet 35, and it faces upward. On the other hand, the board recognition camera 52 is to take an image of various marks, such as a fiducial mark for position recognition and a bad mark provided on the board P as well as to take an image of the respective print positions on the board P when the print state of the board is inspected (print inspection), and it faces downward. These cameras 51 and 52 are incorporated into the camera head 50 in a positional relationship of being vertically symmetrical so that the optical axes are aligned coaxially. This configuration makes it possible to take images of the subject at the same coordinate position on the X-Y coordinate plane from above and below simultaneously.

The cleaner 19 is to clean the mask sheet 35 from the underside as needed and integrally attached to the beam 46 of the imaging unit 18.

The cleaner 19 has a cleaning heat 54 driven to move up and down by an unillustrated driving mechanism. It is configured in such a manner that the cleaning head 54 is set to the ascent position during the cleaning for the cleaning to be performed by bringing the head 46 into sliding contact with the mask sheet 35 in association with the movement of the beam 46. Although it is not shown in detail in the drawing, the cleaning head 54 holds a roll of wiping paper and it is configured in such a manner that residual paste or the like on the mask sheet lower surface and the openings are wiped off by absorbing the residual paste using the wiping paper pulled out from the roll.

Figure 5:
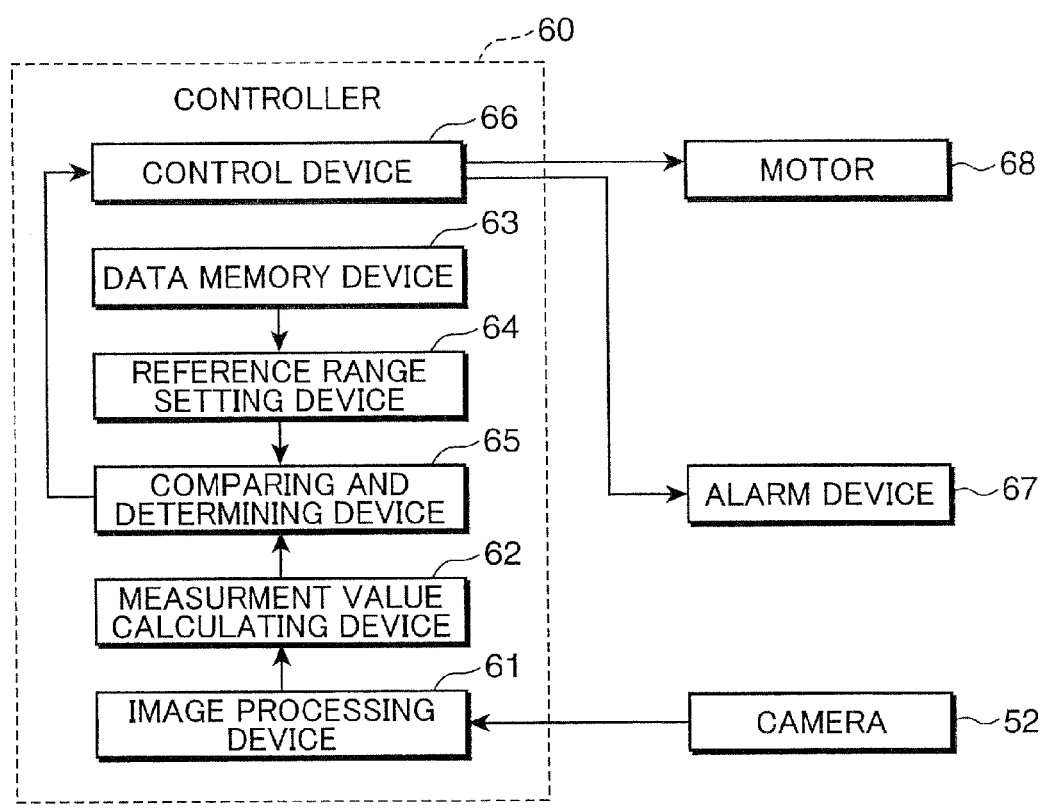
FIG. 5 is a block diagram showing a control system of a print inspection apparatus.

FIG. 5 is a block diagram schematically showing the control system of a print inspection apparatus incorporated into the printer described above.

As is shown in the drawing, a controller 60 provided in the printer includes image processing device 61, measurement value calculating device 62, data memory device 63, reference range setting device 64, comparing and determining device 65, and control device 66, and these device 61 through 66 and the board recognition camera 52 (imaging device) of the imaging unit 18 together constitute the print inspection apparatus.

The image processing device 61 captures an image of the board taken by the board recognition camera 52 after the printing and applies the image processing, such as digitalization, to this image. The measurement value calculating device 62 computes a measurement value of an area of the paste printed on the board on the basis of the image of the board processed by the image processing device 61. The board recognition camera 52, the image processing device 61, and the measurement value calculating device 62 together constitute a measuring device for measuring a quantity (specifically, the area of the paste printed on the board P) relating to an amount of paste printed on the board P.

Meanwhile, the data memory device 63 stores data specifying the reference range for operative condition determination in the terms of the area, and data specifying the range of acceptable product determination. In particular, it stores data specifying a normal reference range used in the other time than the time immediately after the mask sheet cleaning and a special reference range used in the particular time immediately after the mask sheet cleaning as the reference range for operative condition determination.

The reference range setting device 64 reads out a reference range for operative condition determination and a reference range for acceptable product determination from the data memory device 63 and sets the ranges. In particular, it is configured in such a manner that the reference range setting device 64 selects the special reference range in the case of the particular time immediately after the mask sheet cleaning and selects the normal reference range in the case of the other time as the reference range for operative condition determination.

The comparing and determining device 65 compares the reference range for operative condition determination and the reference range for acceptable product determination set by the reference range setting device 64 with the measurement value of the area calculated by the measurement value calculating device 62 to determine whether the measurement value falls with the reference ranges.

The control device 65 also controls an alarm device 67, such as a lamp and a buzzer, provided in the printer 1 and controls various motors 68 and the like provided in the printer 1 according to the determination result by the comparing and determining device 65.

Figure 6A:
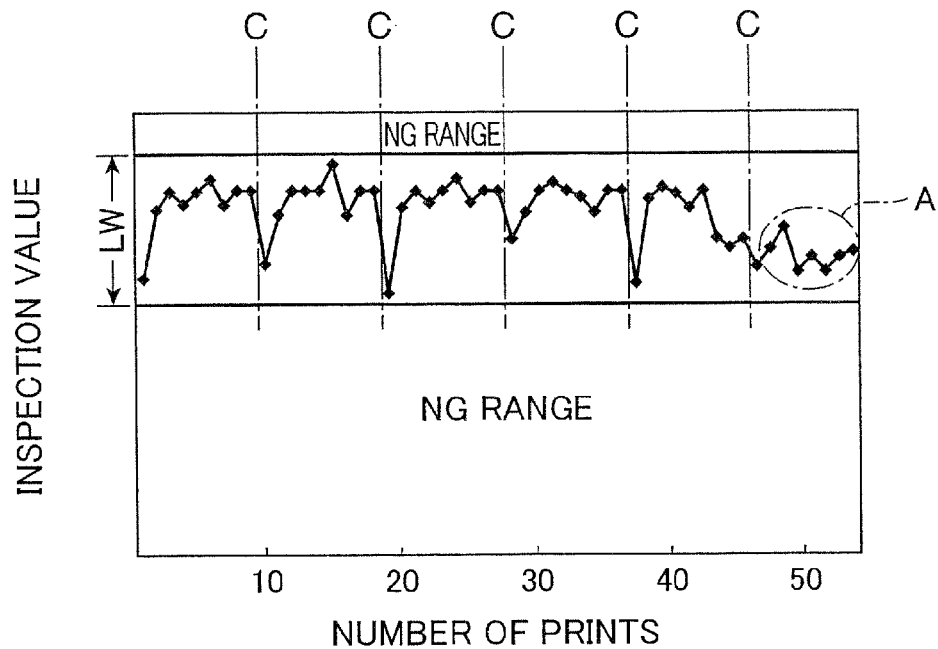
FIG. 6A and FIG. 6B are diagrams having the abscissa referring to the number of prints, showing inspection values (measurement values) of the area of a paste printed on a printed wiring board and a reference range for acceptable product determination and a reference range for operative condition determination.
Figure 6B:
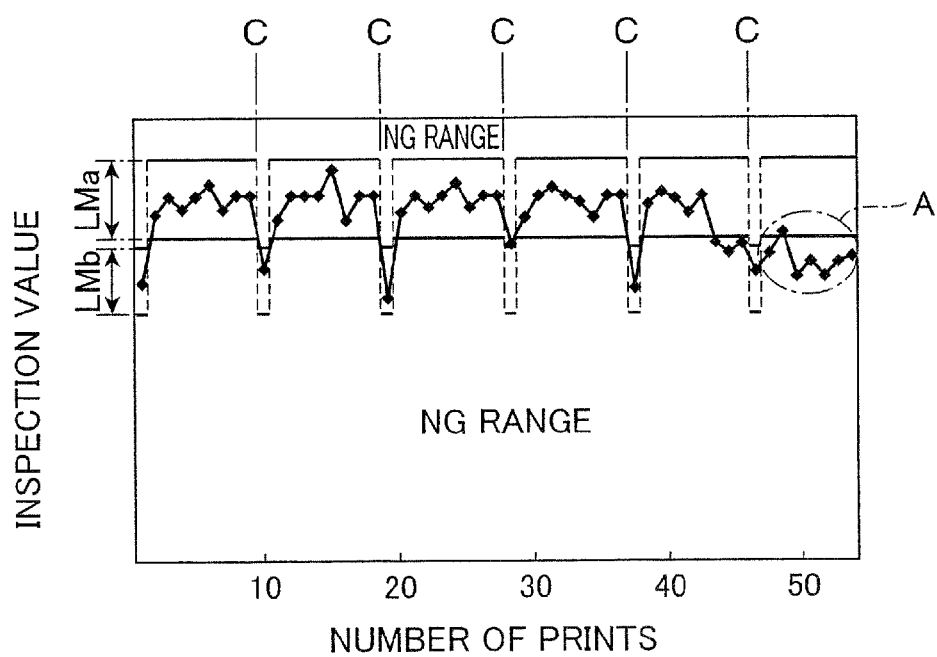

FIG. 6 shows the inspection value (measurement value) of the area of paste printed on the board P using the abscissa referring to the number of prints. A reference range LW for acceptable product determination is shown in FIG. 6A and the reference range (a normal reference range LMa and a special reference range LMb) for operative condition determination is shown in FIG. 6B. The inspection value (measurement value) is a mere example and experimentally examined values are plotted for each number of prints.

In the drawings, a capital C denotes a point in time at which the mask sheet 35 is cleaned by the cleaner 19.

As are shown in these drawings, in a case where the printer is operating normally, the inspection value varies to some extent. Nevertheless, the inspection value is stable so as to fall within an almost constant range except for the particular time immediately after the mask sheet cleaning. On the contrary, the inspection value becomes considerably low immediately after the mask sheet cleaning in comparison with the other time. The reason why is assumed as follows. When printing is performed repetitively after the mask sheet cleaning, paste residue or the like adhering to the mask sheet lower surface resides between the mask sheet 35 and the board Ps, which gives rise to a tendency that the paste slightly seeps out from the openings of the mask sheet 35 during the printing thereafter. The print state is stabilized under such a tendency whereas such a tendency is absent immediately after cleaning.

Accordingly, it is configured in such a manner that, as the reference range for operative condition determination, the normal reference range LMa that is a range to allow a variance in the inspection value in the time except for the time immediately after the mask sheet cleaning in a case where the printer is operating normally, and the special reference range LMb that is a range to allow a variance in the inspection value immediately after the mask sheet cleaning in a case where the printer is operating normally and on the side where an amount of paste is smaller than that in the normal reference range LMa are experimentally found in advance. It is configured in such a manner that the data specifying these reference ranges LMa and LMb is stored in the data memory device 63 and selectively read out by the reference range setting device 64.

The reference range LW for acceptable product determination is defined as a range covering both the two types of reference ranges LMa and LMb for operative condition determination. For example, it is set in a range from the lower limit value of the special reference range LMb to the upper limit value of the normal reference range LMa.

The print inspection method by the print inspection apparatus will now be described with the flow chart in FIG. 7.

When the processing shown in the drawing starts, the board P is carried in first in Step S1, and printing is then performed by the printer 1 in Step S2. In other words, paste is printed on the board P via the mask sheet 35.

After the printing is performed, the reference value LW for acceptable product determination is read out as the processing for print inspection (Step S3) and whether the current moment is immediately after cleaning is determined (Step S4). In a case where it is determined that the current moment is immediately after cleaning, the special reference range LMb is read out and this range is set as the reference range LM for operative condition determination (Step S5). In a case where it is determined that the current moment is not immediately after cleaning, the normal reference range LMa is read out and this range is set as the reference range LM for operative condition determination (Step S6).

Subsequently, in Step S7, the camera head 50 of the imaging unit 18 is activated and an image of the board P after the printing is taken by the board recognition camera 52. The measurement value of the area of the paste printed on the board is then calculated on the basis of the board P whose image has been taken (Step S8).

Subsequently, in Step S9, the measurement value is compared with the reference range LW for acceptable product determination to determine whether the measurement value falls within the reference range LW. In a case where the measurement value is outside the reference range LW, the operation of the printer 1 is stopped and an alarm is given by the alarm device 67 (Step S10).

In a case where the measurement value falls within the reference range LW for acceptable product determination, the measurement value is further compared with the reference range LM for operative condition determination in Step S11. In a case where the measurement value is outside the reference range LM, an alarm is given by the alarm device 67 (Step S12).

In a case where the measurement value falls within the reference range LM for operative condition determination, because the product is an acceptable product and the printer 1 is operating normally, the printer 1 is operated normally and the board P having undergone the print inspection is carried out from the printer 1 (Step S13). Subsequently, whether all the boards 1 of the predetermined number have been printed is determined (Step S14). When not all the boards P have been printed, the processing is repeated from Step S1. When all the boards P have been printed, the processing by this flow is ended.

According to the print inspection apparatus and the print inspection method of this embodiment as described above, the area of paste printed on the board P is measured to compare the measurement value with the reference range LW for acceptable product determination, and in a case where the measurement value is outside the reference range LW (in a case where it falls within an NG range in FIG. 6A), the product is determined as a unacceptable product and the processing for dealing with an occurrence of a unacceptable product (for example, stopping the device and giving an alarm) is performed.

Meanwhile, in a case where the measurement value falls within the reference range LW for acceptable product determination, the measurement value is further compared with the reference range LM for operative condition determination and an alarm is given in a case where the measurement value is outside the reference range LM (in a case where the measurement value falls within an NG range in FIG. 6B). In other words, even when the product is acceptable as an acceptable product, in a case where the measurement value changes from the value of the normal time due to an operative condition change caused by an abnormality or operation defect of the printer 1, for example, when the paste is poured insufficiently or the mask sheet 35 is clogged, such a change is identified and an alarm is given to request the worker to take measures to operate against such a change. It thus becomes possible to forestall the occurrence of an unacceptable product.

In particular, because the reference range LM for operative condition determination is shifted between the time immediately after cleaning and the other time, it is possible to judge an operative condition change more appropriately.

More specifically, as described above, even when the operative condition of the printer 1 is normal, the measurement value may differ between the time immediately after cleaning and the other time. The measurement value in a portion indicated by a capital A in FIG. 6A and FIG. 6B varies toward a paste amount decreasing in comparison with the values in the normal time or the other time than the time immediately after cleaning. This is attributed to an operative condition change of the printer 1 from the normal state. This is on substantially the same as a measurement value obtained immediately after cleaning in the normal operation. Accordingly, in a case where the reference range for operative condition determination is not shifted between the time immediately after cleaning and the other time as with the conventional case, for example, when the range is set in the same manner as the reference range LW for acceptable product determination, it is impossible to distinguish between a change of the measurement value caused by an operative condition change of the printer 1 as is in the portion indicated by a capital A and a change of the measurement value immediately after cleaning in the normal time.

On the contrary, according to the method of this embodiment, the reference range LM for operative condition determination differs between the time immediately after cleaning and the other time and the reference range LMb in the time immediately after cleaning is lower than the reference range LMa in the other time. It is therefore possible to judge a change by distinguishing between a change of the measurement value caused by an operative condition change of the printer 1 and a change of the measurement value immediately after cleaning in the normal time as described above.

It should be appreciated that the specific configurations of the print inspection apparatus and the print inspection method are not limited to the embodiment above and the invention may be modified without deviating from the scope of the invention. For example, the following modifications may be adopted.

Figure 7:
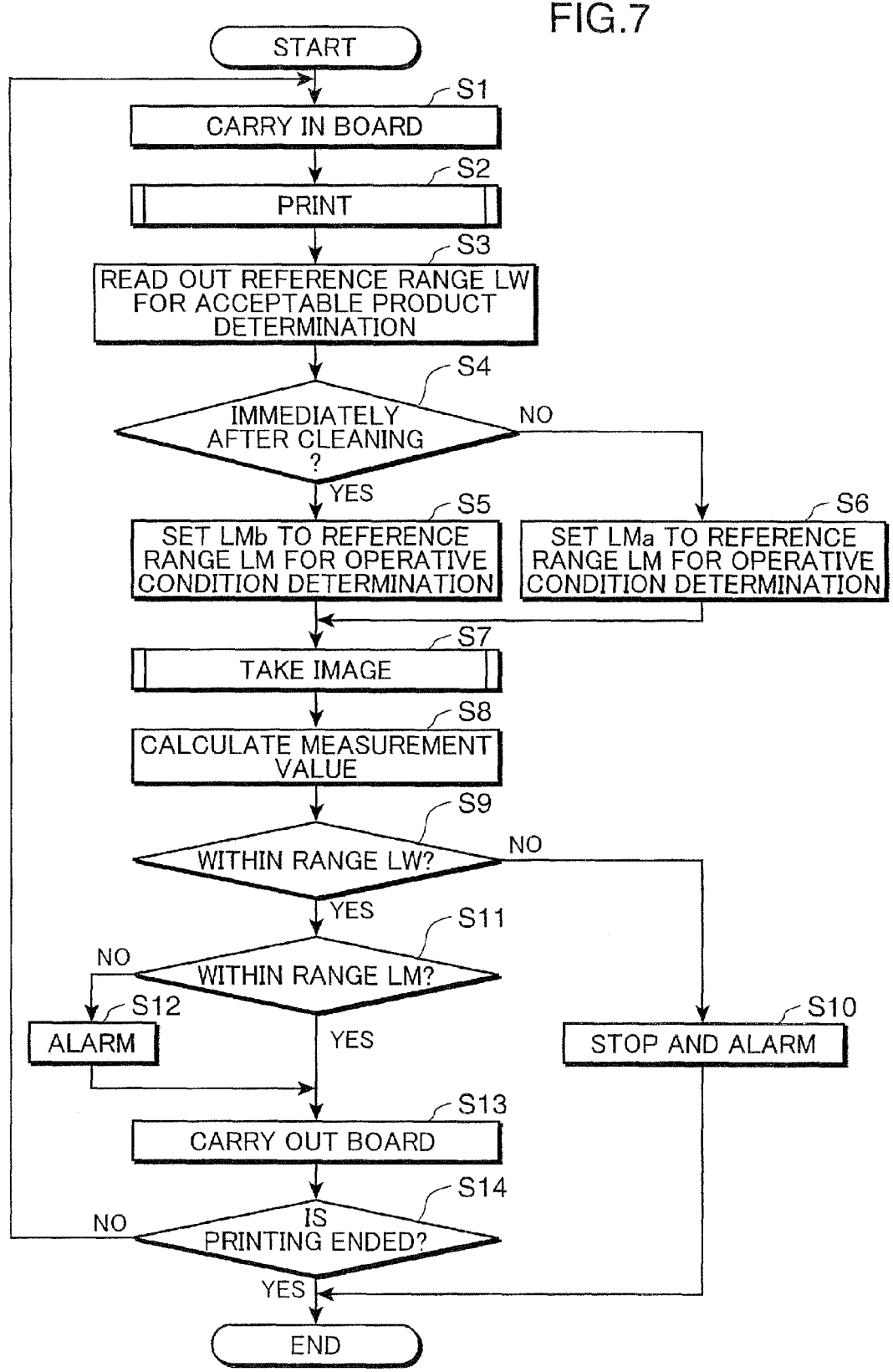
FIG. 7 is a flow chart showing a print inspection method.

(1) The example shown in FIG. 7 is configured in such a manner that in a case where the measurement value is outside the reference range LW for acceptable product determination (in the case of an unacceptable product), the printer 1 is stopped and an alarm is given. However, it may be configured in such a manner that the unacceptable product is sent to an unacceptable product collecting portion.

(2) The reference range LW for acceptable product determination is set in a range from the lower limit value of the reference range LMb to the upper limit value of the reference range LMa of the two types of the reference ranges for operative condition determination in the embodiment above. However, a wider range may be set and the range may be set in response to a request in terms of quality.

(3) The area of printed paste is measured as a quantity in connection with an amount of paste printed on the board P in the embodiment above. However, the volume or the height of printed paste may be measured instead of the area.

(4) According to the printer 1 of the embodiment, the inspection apparatus is integrally incorporated in the printer 1. However, for example, an exclusive-use print inspection apparatus equipped with a camera and movable relatively with respect to the board may be provided separately from the printer 1, so that the board carried out from the printer is carried to the print inspection apparatus to perform the inspection.

The invention described as above can be summarized as follows.

A print inspection method of the invention is adapted for inspecting a paste print state on a printed wiring board after a paste is printed on the printed wiring board via a mask sheet by a printer equipped with the mask sheet, and includes: a measuring step of measuring a quantity in connection with an amount of paste printed on the printed wiring board; and a determining step of comparing a measurement value obtained by measurement with a reference range for operative condition determination to determine whether an operative condition of the printer is normal depending on whether the measurement value falls within the reference range. In the determining step, a special reference range is used for the operative condition determination in a particular time immediately after cleaning of the mask sheet is performed, the special reference range being set for a smaller amount of paste than that for which a normal reference range is set in the other time than the particular time immediately after cleaning.

According to the print inspection method, the quantity is measured after the paste is printed on the printed wiring board. If an operative condition of the printer changes from the normal state, such a change is judged by determining whether the measurement value falls within the reference range for operative condition determination. In particular, because the reference range for operative condition determination is shifted between the time immediately after cleaning and the other time, it is possible to distinguish between a case where the measurement value changes immediately after cleaning while the printer is operating normally and a case where the measurement value changes due to an operative condition change of the printer from the normal state. Accordingly, an operative condition change can be judged more appropriately.

In the method described above, the quantity may be at least one of an area, a volume, and a height of paste printed on the printed wiring board. Also, it may be configured in such a manner that the quantity in connection with the amount of paste printed on the printed wiring board is measured on a basis of an image of the printed wiring board taken after printing by an imaging device.

Meanwhile, a print inspection apparatus of the invention is adapted for inspecting a paste print state on a printed wiring board after a paste is printed on the printed wiring board via a mask sheet by a printer equipped with the mask sheet, and includes: a measuring device for measuring a quantity in connection with an amount of paste printed on the printed wiring board; a reference range setting device for setting a reference range for operative condition determination in the terms of the quantity; and a comparing and determining device for comparing a measurement value by the measuring device with the reference range set by the reference range setting device to determine whether an operative condition of the printer is normal depending on whether the measurement value falls within the reference range. The reference range setting device is configured to selectively set a normal reference range and a special reference range for operative condition determination. The special reference range is set for a smaller amount of paste than that for which the normal reference range is set. The special reference range is set for a particular time immediately after cleaning of the mask sheet is performed, and the normal reference range is set for the other time than the particular time.

According to the print inspection apparatus, the print inspection method described above can be automated and performed effectively.

In the apparatus described above, it may be preferable that the measuring device includes an imaging device for taking an image of the printed wiring board on which the paste has been printed, and a measurement value calculating device for calculating an area of paste having been printed as the quantity on a basis of the image of the printed wiring board.

In this configuration, the measurement value can be found readily at the high accuracy.

Also, it may be preferable to further include an alarm device for giving an alarm in a case where the measurement value is determined to be outside the reference range according to a determination result by the comparing and determining device.

According to this configuration, in a case where the operative condition of the printer varies from a normal state, it becomes possible to notify such a change and deal with such a change.

Also, it may be preferable that the comparing and determining device is configured to compare a reference range for acceptable product determination set in a range covering the normal reference range and the special reference range with a detection value of the quantity in addition to a determination as to whether the operative condition of the printer is normal and to determine unacceptable product when the detection value is outside the reference range for acceptable product determination.

According to this configuration, it is possible to determine both whether the operative condition of the printer is normal and whether the product is acceptable or unacceptable.

Further, a printer of the invention includes: a mask sheet; a print stage located below the mask sheet and configured to support a printed wiring board in a manner so as to allow the printed wiring board to move up and down; a squeegee unit located above the mask sheet and configured to apply a paste; a device for carrying the printed wiring board in and out from the print stage; and the print inspection apparatus described above, whereby a paste print state is inspected after printing for the printed wiring board on the print stage.

According to the printer, it becomes possible to determine an operative condition of the printer by inspecting the print state after the printing is performed until the printed wiring board is carried out.

INDUSTRIAL APPLICABILITY

As has been described, a print inspection method, a print inspection apparatus, and a printer of the invention are useful for a printer that superimposes a printed wiring board and a mask sheet and prints a paste, such as a cream solder, on the printed wiring board via openings formed in the mark sheet, and suitable to maintain a high print quality on the printed wiring board continuously.

The invention claimed is:

1. A print inspection apparatus for inspecting a paste print state on a printed wiring board after paste is printed on the printed wiring board via a mask sheet by a printer equipped with the mask sheet, comprising:
   a measuring device for measuring a quantity in connection with an amount of paste printed on the printed wiring board;
   a reference range setting device for setting a reference range for operative condition determination in terms of the quantity; and
   a comparing and determining device for comparing a measurement value by the measuring device with the reference range set by the reference range setting device to determine whether an operative condition of the printer is normal depending on whether the measurement value falls within the reference range,
   wherein the reference range setting device selectively sets a normal reference range and a special reference range for operative condition determination, and the special reference range is set for a smaller amount of paste than that for which the normal reference range is set, and the special reference range is set for a particular time immediately after cleaning of the mask sheet is performed, and the normal reference range is set for the other time than the particular time.

2. The print inspection apparatus according to claim 1, wherein:
   the measuring device includes an imaging device for taking an image of the printed wiring board on which the paste has been printed, and a measurement value calculating device for calculating an area of paste having been printed as the quantity on a basis of the image of the printed wiring board.

3. The print inspection apparatus according to claim 2, further comprising:
   an alarm device for giving an alarm in a case where the measurement value is determined to be outside the reference range according to a determination result by the comparing and determining device.

4. The print inspection apparatus according to claim 2, wherein:
   the comparing and determining device compares a reference range for acceptable product determination set in a range covering the normal reference range and the special reference range with a detection value of the quantity in addition to a determination as to whether the operative condition of the printer is normal and to determine unacceptable product when the detection value is outside the reference range for acceptable product determination.

5. The print inspection apparatus according to claim 1, further comprising:
an alarm device for giving an alarm in a case where the measurement value is determined to be outside the reference range according to a determination result by the comparing and determining device.

6. The print inspection apparatus according to claim 1, wherein:
the comparing and determining device compares a reference range for acceptable product determination set in a range covering the normal reference range and the special reference range with a detection value of the quantity in addition to a determination as to whether the operative condition of the printer is normal and to determine unacceptable product when the detection value is outside the reference range for acceptable product determination.

7. A printer for printing paste on a printed wiring board, comprising:
a mask sheet;
a print stage located below the mask sheet and configured to support the printed wiring board in a manner so as to allow the printed wiring board to move up and down;
a squeegee unit located above the mask sheet and configured to apply the paste;
a device for carrying the printed wiring board in and out from the print stage; and
a print inspection apparatus including:
a measuring device for measuring a quantity in connection with an amount of paste printed on the printed wiring board;
a reference range setting device for setting a reference range for operative condition determination in terms of the quantity; and
a comparing and determining device for comparing a measurement value by the measuring device with the reference range set by the reference range setting device to determine whether an operative condition of the printer is normal depending on whether the measurement value falls within the reference range,
wherein the reference range setting device selectively sets a normal reference range and a special reference range for operative condition determination, and the special reference range is set for a smaller amount of paste than that for which the normal reference range is set, and the special reference range is set for a particular time immediately after cleaning of the mask sheet is performed, and the normal reference range is set for the other time than the particular time,
whereby a paste print state on the printed wiring board on the print stage is inspected after the printing.

8. The printer according to claim 7, wherein:
the measuring device includes an imaging device for taking an image of the printed wiring board on which the paste has been printed, and a measurement value calculating device for calculating an area of paste having been printed as the quantity on a basis of the image of the printed wiring board.

9. The printer according to claim 8, further comprising:
an alarm device for giving an alarm in a case where the measurement value is determined to be outside the reference range according to a determination result by the comparing and determining device.

10. The printer according to claim 8, wherein:
the comparing and determining device compares a reference range for acceptable product determination set in a range covering the normal reference range and the special reference range with a detection value of the quantity in addition to a determination as to whether the operative condition of the printer is normal and to determine unacceptable product when the detection value is outside the reference range for acceptable product determination.

11. The printer according to claim 7, further comprising:
an alarm device for giving an alarm in a case where the measurement value is determined to be outside the reference range according to a determination result by the comparing and determining device.

12. The printer according to claim 7, wherein:
the comparing and determining device compares a reference range for acceptable product determination set in a range covering the normal reference range and the special reference range with a detection value of the quantity in addition to a determination as to whether the operative condition of the printer is normal and to determine unacceptable product when the detection value is outside the reference range for acceptable product determination.

13. A print inspection method for inspecting a paste print state on a printed wiring board after paste is printed on the printed wiring board via a mask sheet by a printer equipped with the mask sheet, comprising:
a measuring step of measuring a quantity in connection with an amount of paste printed on the printed wiring board; and
a determining step of comparing a measurement value obtained by measurement with a reference range for operative condition determination to determine whether an operative condition of the printer is normal depending on whether the measurement value falls within the reference range,
wherein in the determining step, a special reference range is used for the operative condition determination in a particular time immediately after cleaning of the mask sheet is performed, the special reference range being set for a smaller amount of paste than that for which a normal reference range is set in the other time than the particular time immediately after cleaning.

14. The print inspection method according to claim 13, wherein:
the quantity is at least one of an area, a volume, and a height of paste printed on the printed wiring board.

15. The print inspection method according to claim 14, wherein:
the quantity in connection with the amount of paste printed on the printed wiring board is measured on a basis of an image of the printed wiring board taken by an imaging device.

16. The print inspection method according to claim 13, wherein:
the quantity in connection with the amount of paste printed on the printed wiring board is measured on a basis of an image of the printed wiring board taken by an imaging device.

* * * * *